United States Patent
Caillouette

[19]

[11] Patent Number: 5,928,165
[45] Date of Patent: Jul. 27, 1999

[54] PH MEASUREMENT OF BODY FLUID

[76] Inventor: James C. Caillouette, 685 Oak Knoll Cir., Pasadena, Calif. 91106

[21] Appl. No.: 08/862,032

[22] Filed: May 22, 1997

Related U.S. Application Data

[63] Continuation-in-part of application No. 08/810,347, Mar. 3, 1997, Pat. No. 5,738,634, which is a continuation-in-part of application No. 08/376,830, Jan. 23, 1995, Pat. No. 5,664, 579, which is a continuation-in-part of application No. 08/295,399, Aug. 25, 1994, Pat. No. 5,425,377.

[51] Int. Cl.$^6$ ........................................ A61B 5/00
[52] U.S. Cl. ............................................. 600/572
[58] Field of Search .................... 600/562, 572, 600/573, 584; 604/1; 33/511, 512, 755, 758–760; 206/363–366, 438, 459.1, 569–571

[56] References Cited

U.S. PATENT DOCUMENTS

| | | |
|---|---|---|
| 2,664,879 | 1/1954 | Hardy . |
| 2,945,491 | 7/1960 | Gibbs . |
| 3,013,656 | 12/1961 | Murphy . |
| 3,037,496 | 6/1962 | Melges . |
| 3,117,569 | 1/1964 | Wegner . |
| 3,319,621 | 5/1967 | Schwerin . |
| 3,507,269 | 4/1970 | Berry . |
| 3,509,872 | 5/1970 | Truhan . |
| 3,777,743 | 12/1973 | Binard et al. . |
| 4,409,182 | 10/1983 | Macklem ................................. 422/61 |
| 4,457,313 | 7/1984 | Alter . |
| 4,820,259 | 4/1989 | Stevens . |
| 4,862,899 | 9/1989 | Bucaro . |
| 5,063,930 | 11/1991 | Nucci . |
| 5,147,288 | 9/1992 | Schiavo . |
| 5,425,377 | 6/1995 | Caillouette . |

OTHER PUBLICATIONS

"Vulvovaginitis", vol. 1, Chapter 37, Ronald M. Meltzer 1994.

"Urinary Incontinence and Related Urogenital Symptoms in Elderly Women", Ulla Molander, Scandinavian Association of Obstetricians and Gynecologists, Supplement 158, vol. 72, 1993.

"Estrogen Deprivation and Vaginal Function in Postmenopausal Women", James P. Semmens, MD, Gorm Wagner, MD 1982.

*Primary Examiner*—Max Hindenburg
*Attorney, Agent, or Firm*—William W. Haefliger

[57] ABSTRACT

In the method for detecting pH of vaginal or urethral moisture, the steps that include providing an elongated first carrier; providing a pH detector on the carrier at an end portion thereof; manipulating the carrier to effect exposure of the detector to vaginal or urethral moisture, thereby to cause the detector to exhibit a color change; and providing a pH correlating color comparison measurement means, in sufficiently close association with the carrier and with the detector to allow visual comparison of the changed color exhibited by the detector with a pH correlated color provided by the measurement means.

26 Claims, 7 Drawing Sheets

PH MEASUREMENT OF BODY FLUID

This application is a continuation-in-part of prior U.S. patent application Ser. No. 08/810,347, filed Mar. 3, 1997, now U.S. Pat. No. 5,738,634, which is a continuation-in-part of prior U.S. patent application Ser. No. 08/376,830, filed Jan. 23, 1995, now U.S. Pat. No. 5,664,579, which is a continuation-in-part of prior U.S. patent application Ser. No. 08/295,399, filed Aug. 25, 1994, now U.S. Pat. No. 5,425,377.

BACKGROUND OF THE INVENTION

This invention relates generally to pH measurement of body fluid, such as vaginal and/or urethral fluid, or moisture, and more particularly, to a rapid, easily performed method of obtaining such measurement.

There is continued need to obtain pH measurement of vaginal fluid, as for example in the determination of whether amniotic fluid has escaped into the vagina, during late pregnancy. Amniotic fluid is normally alkaline, whereas vaginal moisture is normally acidic. This difference enables testing for pH, using a test strip, such as a Nitrazine® strip, typically handled by forceps when inserted into the vagina, urethra or other body openings for pH test purposes; however, the procedure and subsequent procedures to determine acidity or alkalinity requires considerable manipulation, including cutting of a test strip, grasping of the cut strip by forceps manipulation, subsequent insertion with risk of separation of the strip from the forceps, recovery of the strip, and its examination. There is also need to obtain pH measurement of urethral moisture.

There is need for a simple, rapidly carried out method which obviates problems associated with the conventional procedure; also, there is need for ease of excess moisture and mucous removal from the vagina, and/or urethra, at the time of the pH test.

SUMMARY OF THE INVENTION

It is a major object of the invention to provide a significantly improved method which meets the above need, and overcomes prior problems, as referred to. Basically, the method of the invention includes the steps:

a) providing an elongated first carrier, b) providing a pH detector on the carrier at end portion thereof, c) manipulating the carrier to effect exposure of the detector to vaginal or urethral moisture, thereby to cause the detector to exhibit a color change, d) providing a pH correlating color comparison measurement means, in sufficiently close association with the carrier or on the package and with the detector to allow visual comparison of the changed color exhibited by the detector with a pH correlated color provided by the measurement means.

Another object is to provide a package for supporting the first carrier and the color comparison measurement means. In this regard provision may be made for removable containment of the first carrier by the package.

A further object is to provide the detector in the form of an elongated strip, the color comparison measurement means being provided in the form of a strip of material that is elongated in a direction related to the elongated direction of said detector strip to facilitate the color comparison. A method of use typically includes relatively moving the color comparison measurement means and the carrier to achieve the close association of the color comparison measurement means with the detector.

Yet another object includes providing the color comparison measurement strip on the carrier to have thickness that is everywhere less than the thickness of the carrier adjacent the measurement strip. The color comparison measurement strip may be adhered to a package for the pH detector strip on the carrier.

An additional object includes providing the color comparison measurement strip to exhibit a series of colors spaced linearly, and wherein that strip may be located in such relation to said carrier as to position the linearly spaced series of colors in parallel with the elongated detector strip.

A yet further object is to provide the color comparison measurement means on a second carrier that extends at least part way about the first carrier, and to provide the second carrier with a transparent zone to allow visual observation of the detector strip moved into registration with that zone. The second carrier may be provided to have an elongated storage receptacle into which said first carrier, such as a carrier stick, is substantially completely receivable and from which the first carrier is removable to allow its manipulation. That receptacle may provide the transparent zone proximate said color comparison measurement means, to allow ready observation of the detector strip through that zone, for color comparison.

An auxiliary object is to provide a method which includes the steps:

a) providing a pH indication, color comparison measurement, and swabbing means on a carrier stick, b) manipulating the stick between its opposite ends to obtain pH indication of vaginal or urethral moisture at one end of the stick, c) visually interpreting that indication to also obtain pH measurement of such moisture near that one end of the stick, d) again manipulating the stick between its opposite ends, to swab the cervix or urethra, e) and disposing of the stick, whereby disposition of the pH indication, measurement and swabbing means is thereby obtained in one disposal step.

In this regard, the disposal of such a stick may include inserting it into a transparent receptacle, that enables viewing of the pH indication means and color comparison means, protected in the receptacle. A kit may be provided including a support for one such receptacle to receive the carrier stick for the detector, as well as a second receptacle on the support for a second carrier stick, one in which the swab is removably received. The pH indication means on the two sticks may be respectively used to obtain pH indications from vaginal and urethral mositure zones, for comparison check.

As will appear, the a) step may include adhering a pH indication strip to one end of the stick and adhering a pH measurement calorimeter strip to the stick adjacent the pH indication strip, but between the indication strip and the swabbing means, leaving stick extent free for manual manipulation.

A smooth surfaced protective tip may be provided at the strip end of the stick, to facilitate comfortable insertion of that end of the stick in the vagina or urethra, and that tip may be provided in the form of a slotted sleeve fitted over or endwise adjacent the indicator strip. The indicator strip may have a micro-pore cover layer.

It is another object to provide pH measurement means having color gradations in a series sequence, including locating the series lengthwise along the stick, adjacent the indication means. As will be seen, pH measurement means may be provided by winding it about one end of the stick.

A further object includes maintaining an elongated gap along the stick between the pH measurement means and the swabbing means, whereby the stick may be grasped at the gap for manipulation. In this regard, the swabbing means may be provided by attaching a moisture-absorbing swab to the other end of the stick, and in lengthwise spaced relation to both pH indicating means and pH measurement means. The swab may contain an antiseptic or anaesthetic substance.

Yet another object includes the provision of the pH measurement means to have a pH numerical sequence in a series associated with the color gradations, and including also locating the numerical sequence lengthwise along the stick. Apparatus incorporating the invention includes, in combination a) an elongated stick,
b) pH indicating first means on the stick, at one end portion thereof,
c) color comparison pH measurement second means, the stick movable relative to the second means to bring the first means into registration with the second means, for color comparison.

The first means typically comprises a strip adhered to one end of the stick, and the second means may extend lengthwise relative to the stick, and the second means typically has color gradations in a series sequence lengthwise relative to the stick.

An additional object includes the provision of a package for the pH detector strip and stick, and also carrying the color comparison measurement means, as referred to. The package may also provide for packaging of the swab.

These and other objects and advantages of the invention, as well as the details of an illustrative embodiment, will be more fully understood from the following specification and drawings, in which:

DETAILED DESCRIPTION

In the drawings, an elongated, narrow carrier stick 10 may consist of wood, plastic, or other material. Provided on the carrier stick are:

a pH indication means, as generally shown at 11, at one end portion 10a of the stick;

a color comparison pH measurement means, as generally indicated at 12, spaced from stick end portion 10a, but close to 11; and a swabbing means, as generally indicated at 13 on the opposite end portion 10b of the stick.

As shown, the first means 11 may comprise a pH indication strip, such as a Nitrazine® strip, wound about the stick end portion 10a and adhered to same as by an adhesive. The color comparison pH measurement means 12 may comprise a thin paper strip adhered to the stick surface to extend lengthwise of the stick from the edge or end 11a of the first means 11. The second means is shown to have color gradations in a series sequence, as in colored bands 12a, positioned lengthwise of or along the stick. In addition, the paper strip 12 may include pH numerical indicators 12b along side the color gradation bands, to enable:

visual color comparison of the pH indication means 11 (immediately after its exposure to vaginal fluid) with the bands 12a, for visual selection of that band most close in color to the color of the indication means 11; and immediate visual readout of the pH number adjacent the selected band.

The stick projects freely at 10c away from the first and second means 11 and 12 for manual manipulation (see the grasping finger and thumb 18 and 19), to first obtain pH indication of vaginal or urethral moisture at one end of the stick, and to enable visual interpretation of that indication by color comparison with the second means, without manual release of the stick. The stick is then disposable, or may be disposed of, after a swabbing step to be described.

The swabbing means 13 may comprise a soft cotton swab, or other absorbent material, attached to the carrier stick at its opposite end, and in spaced relation to the first and second means 11 and 12. The lengthwise spacing "d" between 13 and 12 is such as to enable free manual manipulation of the stick; and such spacing is typically between 3 and 5 inches, enabling ready finger grasping of the stick and manipulation thereof, including rapid endwise reversal of the stick. In a specific example "d" is about 4 inches, and the stick diameter is about ⅜ inch.

The method of measuring pH of vaginal or urethral moisture includes the steps:

a) providing a pH indication, color comparison measurement, and swabbing means on a carrier stick, b) manipulating the stick between its opposite ends to obtain pH indication of vaginal or urethral moisture at one end of the stick, c) visually interpreting that indication to also obtain pH measurement of such moisture near that one end of the stick, d) again manipulating the stick between its opposite ends, including endwise reversing it, to swab the vaginal cavity or the urethra in the area from which pH indication was obtained, e) and disposing of the stick, whereby disposition of the pH indication, measurement and swabbing means is thereby obtained in one disposal step.

The overall sizes of 11, 12 and 13 are such as to enable ready insertion into the vagina or urethra, via stick manipulation at zone 10c, with ready stick reversal, as needed. Swabbing of the vagina or urethra indicated at 22 is typically carried out in conjunction with pH measurement, via stick manipulation and endwise reversal, to obtain best measurement results.

Figure 5:
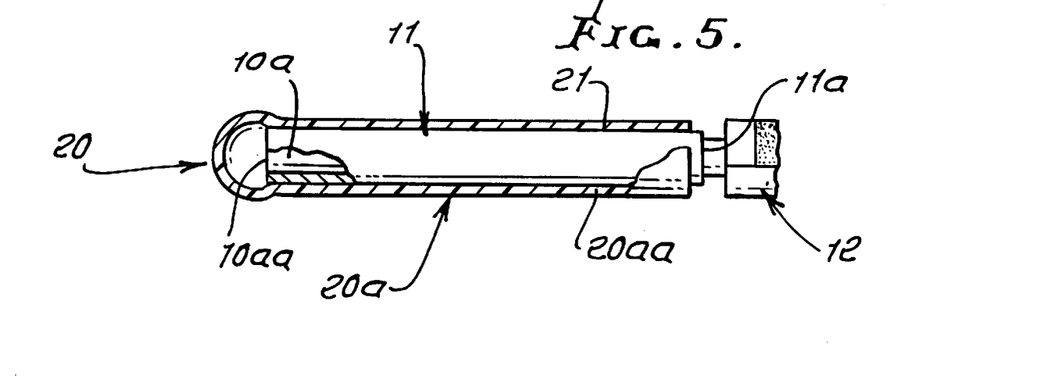
FIG. 5 is an elevation, partly in section, showing a modification.
Figure 6:
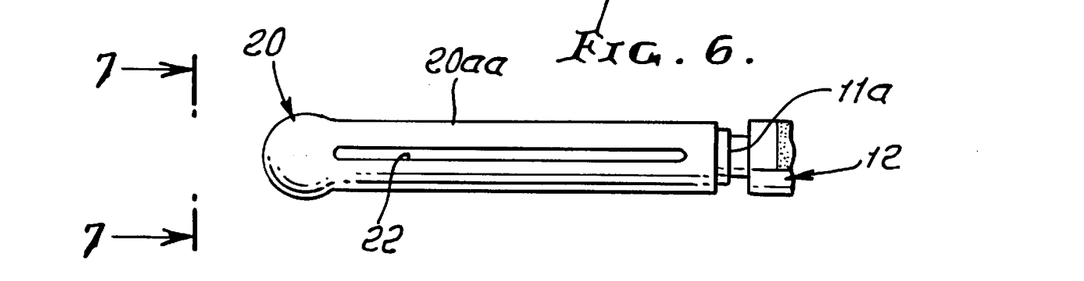
FIG. 6 is a side elevation of the FIG. 5 modification.
Figure 7:
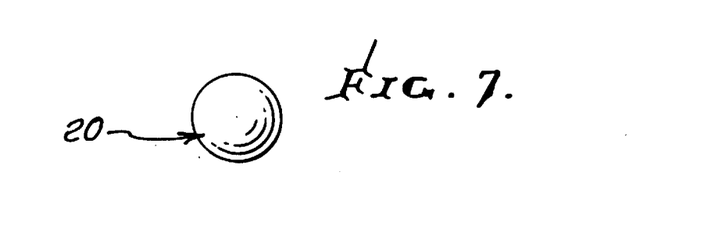
FIG. 7 is an end view taken on lines 7—7 of FIG. 6.

Referring now to the modification shown in FIGS. 5–7, a smooth surfaced protective tip 20 is provided to face endwise at the end 10aa of the stick end portion 10a. As shown, the tip 20 is endwise convex, as for example bulbous, to provide for or enable comfortable insertion of the stick end portion 10a into the vagina or urethra, for pH measurement. The tip 20 may typically be formed integrally with a sleeve 20a assembled over and closely fitting the measurement strip 11, and may be suitably adhered thereto, locally, as at 21. A suitable bonding agent is epoxy. The remainder of the strip 11 is therefore available for pH indication. Alternatively, the sleeve may be attached, as by heat shrinking, or by wedge fit.

A fluid access opening is provided through the wall of the sleeve, whereby vaginal or urethral moisture or fluid may access the strip 11 via that opening. See for example elongated slot 22 in the sleeve wall 20aa. The sleeve and tip may consist of transparent, molded, plastic material, to facilitate viewing of a change of color of the strip 11.

Figure 8:
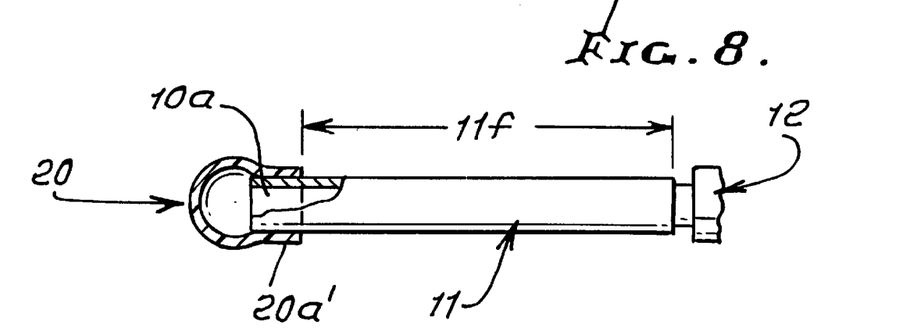
FIG. 8 is an elevation showing a further modification.

In FIG. 8, the sleeve 20a is shortened and tapered at sleeve end 20a' into flush, or near flush, relation with the surface of the strip, at a locus on stick end portion 10a. This leaves the remaining length 11f of the strip openly exposed for moisture contact.

Figure 9:
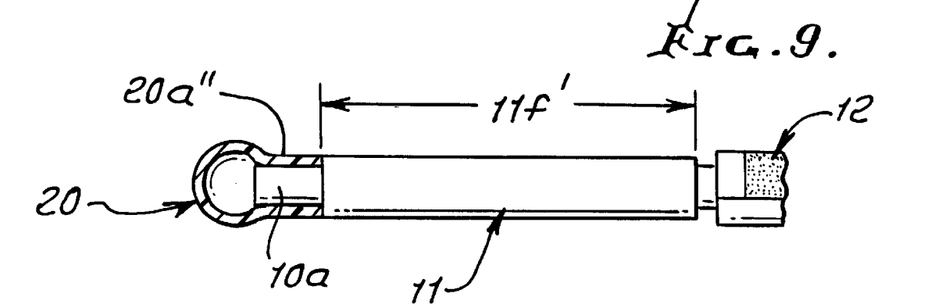
FIG. 9 is an elevation showing yet another modification.

In FIG. 9, the sleeve 20a'' is also shortened and attached to the stick end portion 10a, and in endwise alignment with the strip 11. This also leaves the remaining length 11f' of the strip openly exposed for moisture contact.

Figure 10:
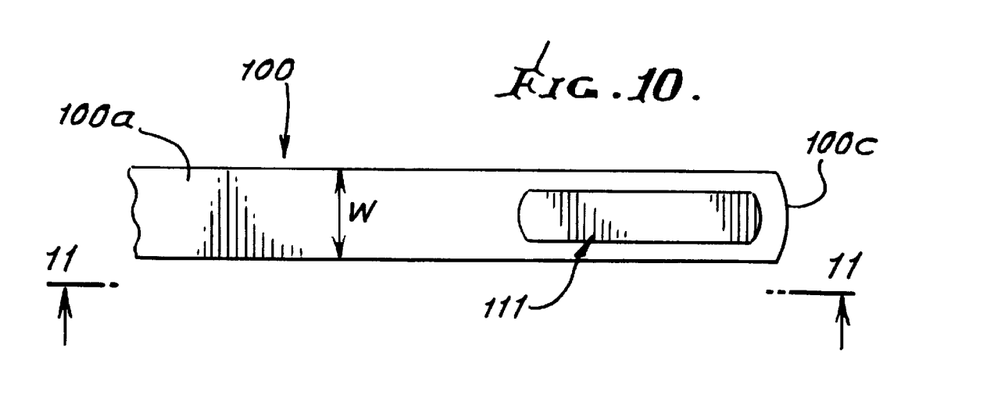
FIG. 10 is a plan view of a modified carrier stick, with a pH detector strip on its surface.
Figure 11:
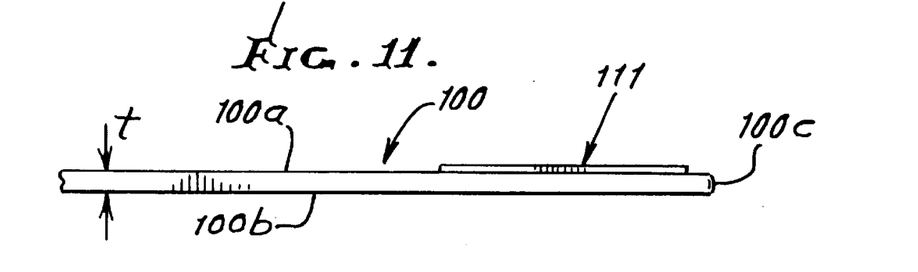
FIG. 11 is an edge view taken on lines 11—11 of FIG. 10.
Figure 12:
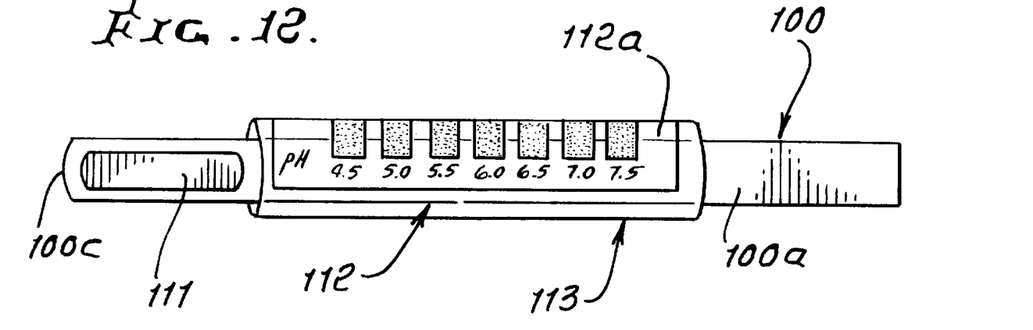
FIG. 12 is a view like FIG. 10, but showing a second carrier extending about the stick of FIG. 10, and relatively slidable lengthwise, the second carrier carrying color comparison measurement elements.

In FIGS. 10–12, a carrier stick 100 may consist of wood, plastic or other material. It is elongated, and has width "w" and thickness "t", where w exceeds t. The stick has flat opposite sides 100a and 100b, and a smoothly rounded or curved forward end 100c to be inserted into a body cavity, as described above. An elongated pH detector is carried by the stick 100, and may take the form of a Nitrazine® strip 111 adhered to the side 100a of the stick, near convex end 100c, as shown. Typically, strip 111 is thinner than stick thickness "t". Stick 100 enables ease of manipulation to effect exposure of the detector to vaginal or urethral moisture, thereby to cause the detector strip to exhibit color change.

A pH correlating color comparison measurement means is provided in sufficiently close association with said carrier and with said detector to allow visual comparison of the changed color exhibited by said detector with a pH correlated color provided by said measurement means. See for example the second carrier 113 for the color comparison means 112, the carrier 113 being in the form of a sleeve extending at least part way about the stick 100 as seen in FIG. 12. The color comparison means 112 is shown in the form of a series of bands, each having a different color corresponding to a pH level color to which the detector strip may change. See for example the indicated pH levels 4.5, 5.0, 5.5, 6.0, 6.5, 7.0 and 7.5 adjacent the color bands. The bands may be provided on a strip 112a adhered to the sleeve 113. Paper strips providing such elements are known, and sold under the name HYDRION. The band for pH 4.5 is typically bright yellow; the band for pH 6.0 is olive in color; and the band for pH 7.5 is navy blue.

Figure 13:
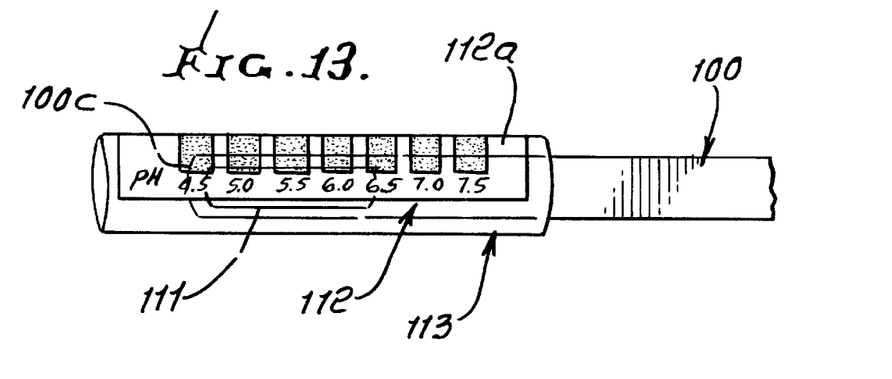
FIG. 13 is a view like FIG. 12 showing the measurement elements registering with the pH detector strip.

In use, the stick 100 and sleeve 113 are relatively moved, lengthwise, to bring the detector strip 11 (after its exposure to moisture and color change as referred to above) into lateral registration with the color comparison bands, enabling ready visual comparison of the color of the detector strip with the closest color of one of the bands, enabling a pH determination. See FIG. 13. For this purpose, a zone of the carrier sleeve adjacent the bands may be transparent to allow visual observation of the detector, through that zone, adjacent the bands. The entire sleeve and the strip 112a may be transparent.

Figure 14:
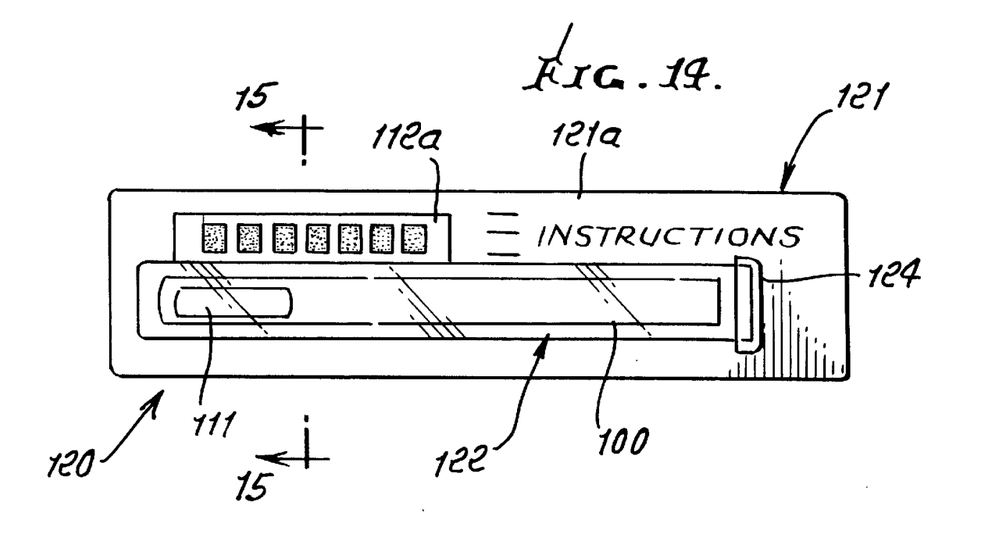
FIG. 14 is a plan view of a modification wherein a carrier stick for a pH detector strip is removably contained in a transparent sleeve on a support or substrate, with a color comparison measurement strip also mounted on the support.
Figure 15:
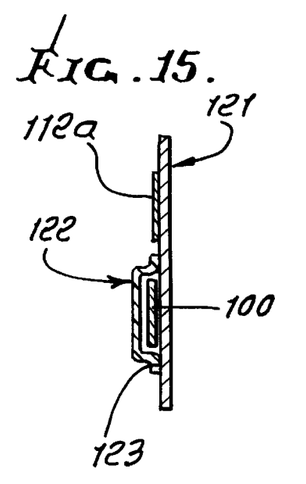
FIG. 15 is an enlarged section taken on lines 15—15 of FIG. 14.

FIGS. 14 and 15 show a package 120 for the stick 100, detector 111 and color comparison measurement strip 112a that provides the color comparison bands, as referred to. This form of the invention is preferred, although the other forms as described are also desirable and useful.

The package 120 may include a support or substrate 121, such as a cardboard base strip, having a white or other light colored upper surface 121a. A transparent plastic elongated receptacle 122 is mounted on the base, as at 123, and removably receives the stick 100 and detector 111. A cap 124 at the end of the receptacle remote from the detector may be removed to allow stick removal for manipulation as described, to expose the detector to moisture the pH of which is to be determined.

The color comparison measurement strip 112a is adhered to the upper surface of the base. Note that it may be located as shown, proximate the exposed detector 111 as received or re-inserted into the receptacle, after use of the detector. Therefore, a ready, visual, side-by-side comparison of the color of the detector with the color of the bands on strip 112a may be made, and the stick and detector are simultaneously contained, as against contamination, before and after removal for manipulation and use.

Figure 16:
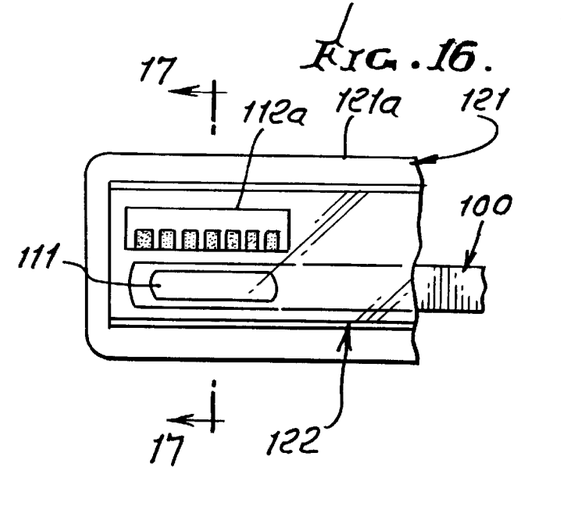
FIG. 16 is a view like FIG. 14, but showing a modification.
Figure 17:
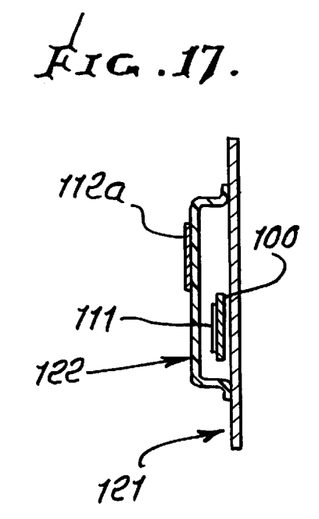
FIG. 17 is a section taken on lines 17—17 of FIG. 16.

FIGS. 16 and 17 show a modified form, which is like FIG. 14, except that color measurement strip 112a is adhered to the transparent plastic, elongated receptacle 122 to be closer to the detector 111 on stick 100 received in the receptacle 122.

Figure 18:
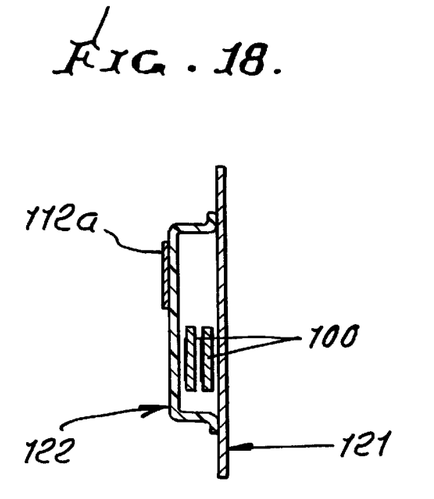
FIG. 18 is a view like FIG. 17, showing a modification.

FIG. 18 is like FIG. 17, except that the receptacle receives two like sticks 100, each with a detector strip 111 thereon. A redundancy or validity check may be made by use of both sticks to obtain moisture on the detector as from different surface zones of the vagina, or urethra, or from one zone at the vagina, and the other at the urethra, for comparison with the colored bands on color comparison strip 112a.

Figure 1:
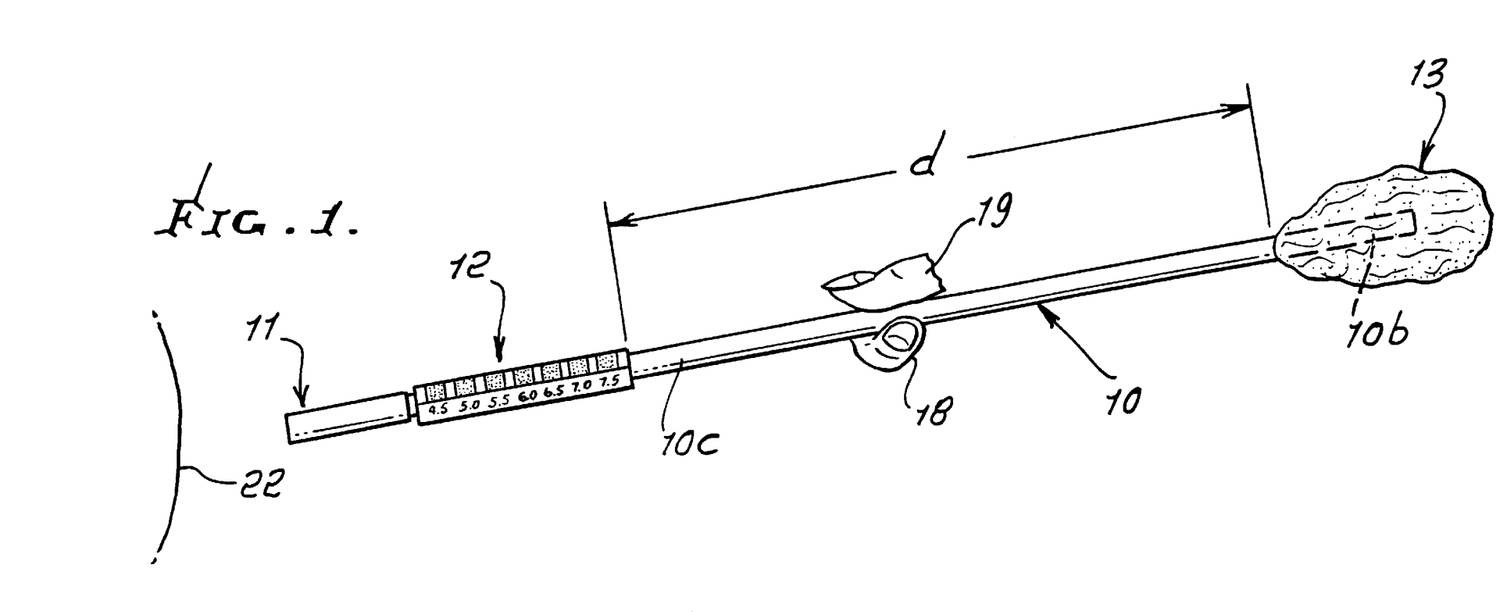
FIG. 1 is a side elevational view of stick apparatus incorporating the invention.
Figure 2:
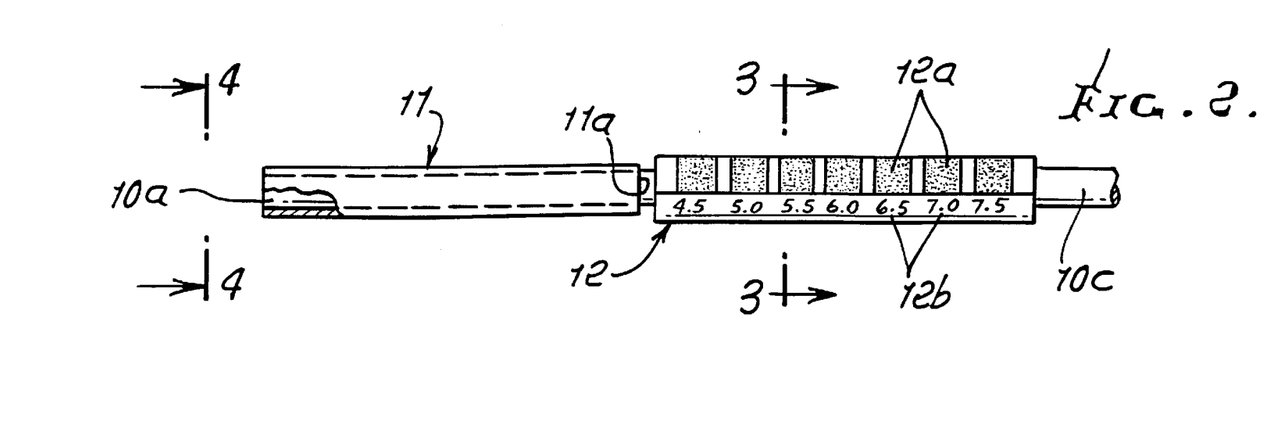
FIG. 2 is an enlarged side view of one end portion of the FIG. 1 stick apparatus.
Figure 3:
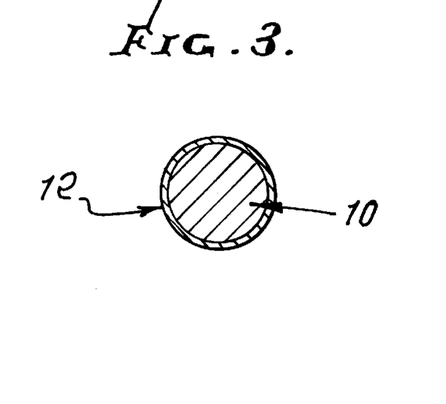
FIG. 3 is an enlarged section taken on lines 3—3 of FIG. 2.
Figure 4:
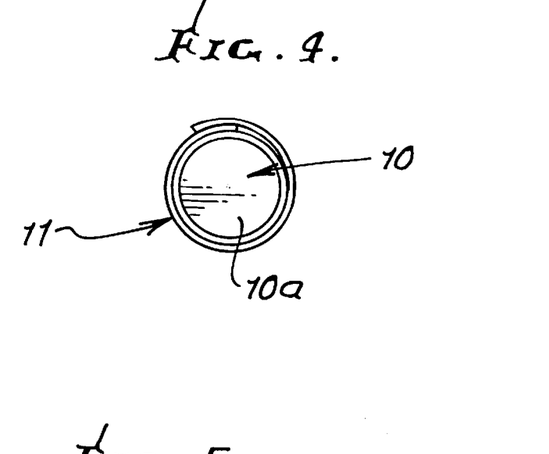
FIG. 4 is an enlarged end view taken on lines 4—4 of FIG. 2.
Figure 19:
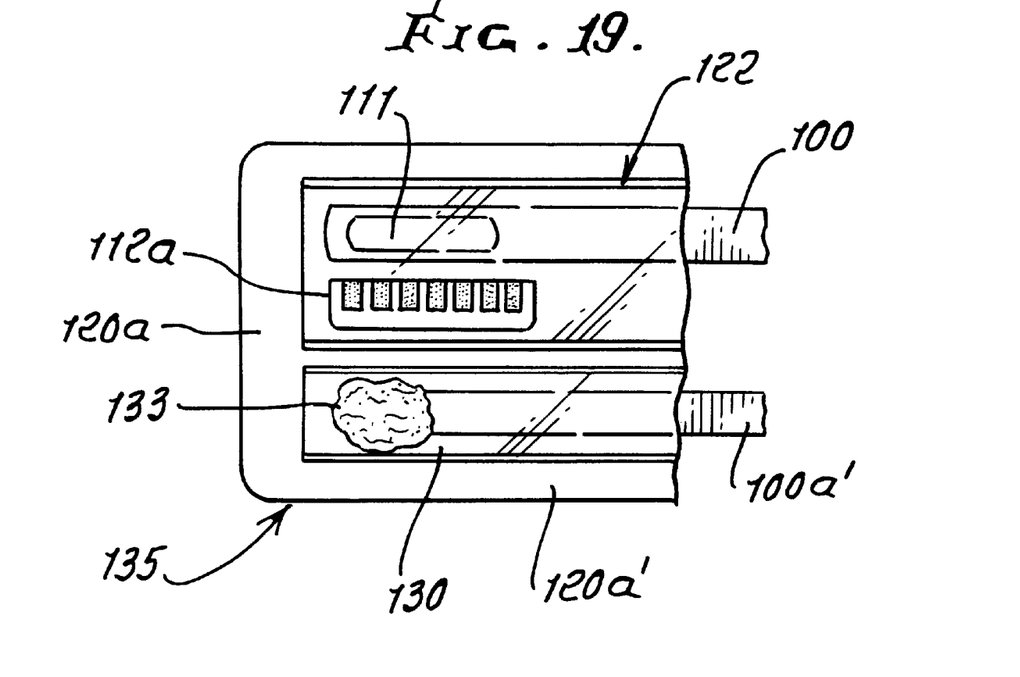
FIG. 19 is a view like FIG. 16, showing a further modification.

FIG. 19 shows still another form of the package, the upper portion of which is like that shown in FIG. 17. See identical numerals. The modified package 135 includes a wider base or support 120a, as at 120a', to mount or carry a second transparent plastic receptacle 130. A second stick 100a' has an end swab 133, like swab 13 in FIG. 1 and used for the same purpose. Therefore, a kit is provided to enable pH determination, as well as enable vaginal or urethral swabbing, if desired.

It is contemplated that the swab 133 itself may be treated, or carry, pH detector substance, to change color in accordance with the pH of the moisture it contacts. Therefore, in the FIG. 19 device, the swab 133 acting as a detector, may be compared with the color bands on strip 112a.

Figure 20:
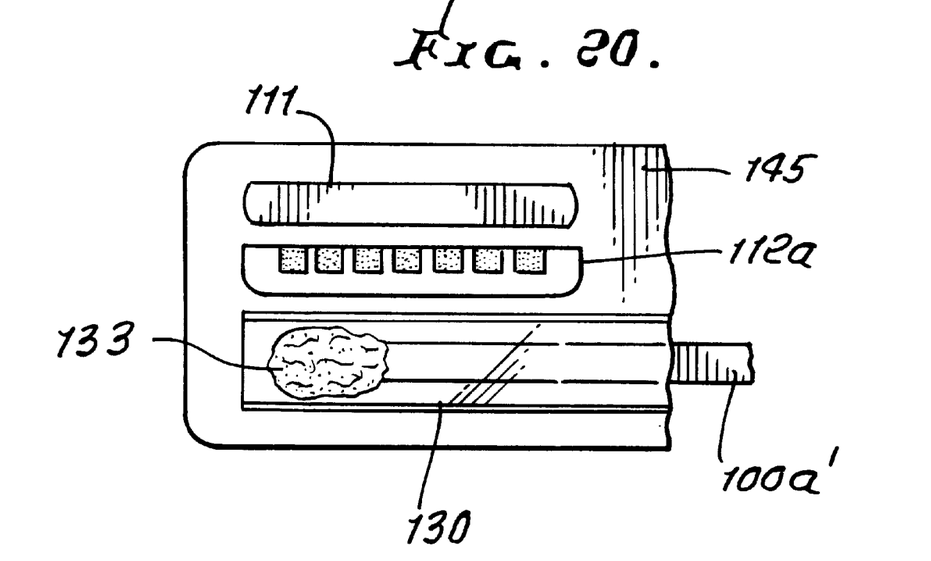
FIG. 20 is a view like FIG. 19 showing a further modification.

FIG. 20 shows a further kit modification, whereon a swab 133 is carried on a stick 100a in a receptacle as at 130, in FIG. 19. The receptacle 122 is not used. Detector strips 111 and color comparison measurement strip 112a are both adhered to the support 145, and in side-by-side relation. In use, the swab 133 is removed from 130 and manipulated on its stick 100a' to become moist due to pick-up of vaginal or urethral moisture. The moist swab 133 is then "swabbed" or rubbed onto detector strip 111, which duly changes color according to pH of the transferred moisture. The color of strip 111 can then be compared to colors on strip 112a.

Figure 21:
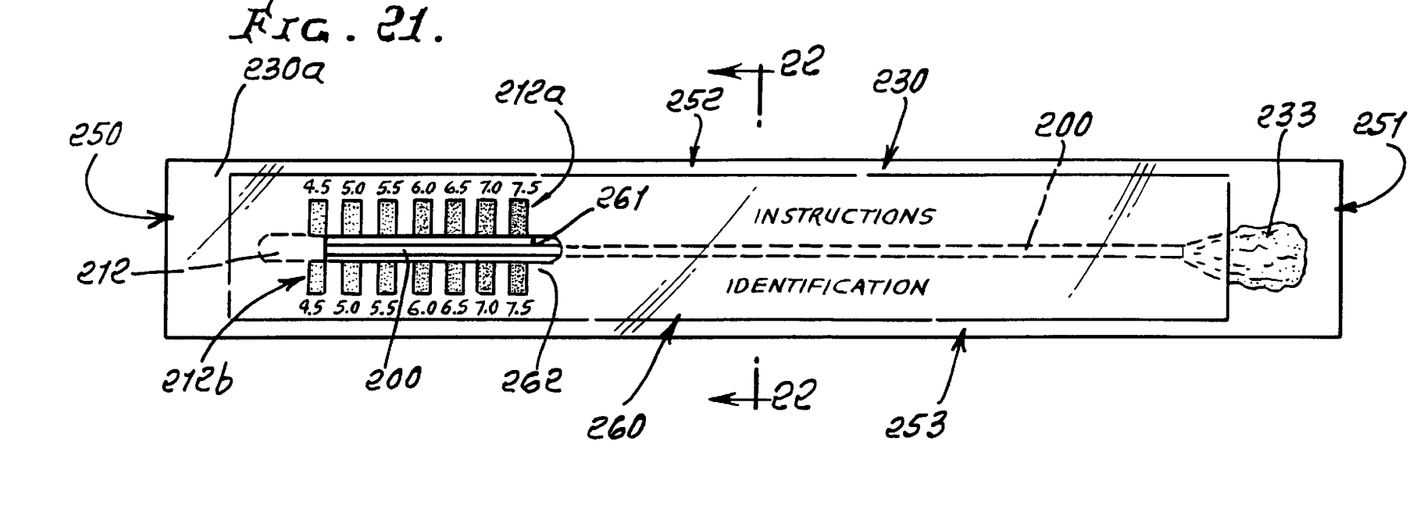
FIG. 21 is a view like FIG. 16 showing another modification.
Figure 22:
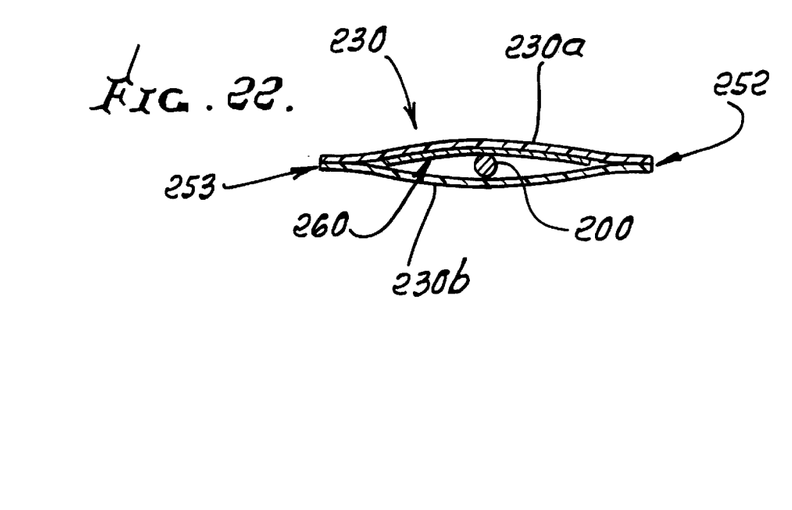
FIG. 22 is a section taken on lines 22—22 of FIG. 21.

FIGS. 21 and 22 show yet another kit modification in which an indicator strip or tip 212 (corresponding to strip or tip 111) is carried at the left end of elongated stick 200. A swab 233 is carried at the right end of the stick. An encapsulating, thin, flexible, transparent receptacle 230 protectively contains the elongated stick, tip 212 and swab 233, and may be torn open to retrieve the stick. The receptacle may consist of thin walled plastic sheets 230a and 230b bonded together along sheet edge portions indicated at 250, 251, 252 and 253, whereby the receptacle is sealed.

A thin, elongated paper insert sheet 260 is also received in the receptacle, to overlie most of stick 200, whereby use instruction and identification data may be printed on the sheet 260 and presented upwardly or outwardly for viewing through the transparent upper sheet 230a. Sheet 260 defines a narrow window or cut-out at 261, which is elongated along a mid-portion 262 of sheet 260, as shown.

Color comparison elements such as bands are carried by the insert sheet 260, as in two rows shown at 212a and 212b, at opposite sides of the window. Preferably, the longitudinally spaced bands extend to laterally spaced edges of the window, for ease of color comparison of the indicator (after its exposure to moisture as described above) with the different bands.

Longitudinally spaced bands have different colors, while laterally oppositely spaced bands have the same color. Note their pH numerical labeling, at 4.5, 5.0, 5.5., 6.0, 6.5, 7.0, and 7.5, along the window length.

In use, the right end of the receptacle is opened, and the carrier stick 200 is withdrawn, for use. Thereafter, the indicator tip 212, which may be cylindrical, after its exposure to moisture, is reinserted into the elongated receptacle 230, under the insert sheet 260, to bring tip 212 under the window 261. Tip 212 preferably has a width or diameter greater than the window width, so that it adjacently registers with the successive bands in the two rows as the tip moves longitudinally. This facilitates ease of color comparison of the tip with the bands. After such color comparison use, the tip and stick remain in the receptacle, for ease of disposal. As an alternative, the insert sheet 260 may be omitted, and the two rows of bands 212a and 212b may be printed directly on the receptacle sheet 230a, which is transparent. Therefore, a window is formed by that portion of sheet 230a between the laterally spaced bands.

The disclosures of applicant's pending applications Ser. No. 08/570,534 filed Dec. 11, 1995, and Ser. No. 08/699,251 filed Aug. 19, 1996 are incorporated herein, by reference.

I claim:

1. In the method for detecting pH of vaginal or urethral moisture, the steps that include a) providing an elongated first carrier,
b) providing a pH detector on the carrier at an end portion thereof,
c) manipulating said carrier to effect exposure of said detector to vaginal or urethral moisture, thereby to cause said detector to exhibit a color change,
d) providing a pH correlating color comparison measurement means, in sufficiently close association with said carrier and with said detector to allow visual comparison of the changed color exhibited by said detector with a pH correlated color provided by said measurement means,
e) providing a longitudinally elongated receptacle for said carrier and detector, said color comparison measurement means provided in association with the receptacle and relative to which the carrier and detector are relatively longitudinally manipulatively movable for visual color comparison with said color comparison measurement means.

2. The method of claim 1 wherein said receptacle defines a package for supporting said first carrier and said color comparison measurement means.

3. The method of claim 2 including providing for removable containment of said first carrier by said package.

4. The method of claim 1 wherein said detector is provided in the form of an elongated strip and said color comparison measurement means is provided in the form of a strip of material that is elongated in a direction related to the elongated direction of said detector strip to facilitate said color comparison.

5. The method of claim 4 wherein said receptacle defines a package for said carrier, and adhering said color comparison measurement strip to said package.

6. The method of claim 2 wherein said color comparison measurement strip exhibits a series of colors spaced apart linearly, and including locating said color comparison measurement strip in such relation to said carrier as to position said linearly spaced series of colors in parallel with said elongated detector strip.

7. The method of claim 1 wherein said detector is provided in the form of an elongated strip, and said color comparison measurement means is provided on a second carrier that is movable relative to and lengthwise of the first carrier.

8. The method of claim 7 wherein said second carrier is provided to have a portion that extends at least part way about the first carrier.

9. In the method for detecting pH of vaginal or urethral moisture, the steps that include a) providing an elongated first carrier,
b) providing a pH detector on the carrier at an end portion thereof,
c) manipulating said carrier to effect exposure of said detector to vaginal or urethral moisture, thereby to cause said detector to exhibit a color change,
d) providing a pH correlating color comparison measurement means, in sufficiently close association with said carrier and with said detector to allow visual comparison of the changed color exhibited by said detector with a pH correlated color provided by said measurement means,
e) said detector provided in the form of an elongated strip, and said color comparison measurement means is provided on a second carrier that is movable relative to and lengthwise of the first carrier,
f) and wherein said second carrier is provided to have a transparent zone to allow observation of said detector strip through said zone.

10. The method of claim 12 wherein said second carrier is provided in the form of an elongated storage receptacle into which said first carrier is substantially completely receivable and from which the first carrier is removable to allow its manipulation.

11. The method of claim 10 wherein said receptacle is provided to have a transparent zone proximate said color comparison measurement means to allow observation of said strip through said zone, for said color comparison.

12. In combination:
   a) a support package,
   b) a carrier and a pH detector on the carrier, the carrier removably supported by the package,
   c) color comparison measurement elements carried by the package to allow their comparison with said pH detector after exposure of said detector to vaginal or urethral moisture the pH of which is to be determined,
   d) said package including a longitudinally elongated receptacle for said carrier and detector, said elements located in association with said receptacle and relative to which the detector and carrier are relatively longitudinally manipulatively movable for visual color comparison with said elements.

13. The combination of claim 12 wherein the package includes a support base and said receptacle on the base, the carrier and pH detector removably received in the receptacle.

14. The combination of claim 13 wherein the color comparison measurement elements are on one of the following:
   i) the support base
   ii) the receptacle.

15. The combination of claim 13 wherein the receptacle is sufficiently transparent to allow viewing of the detector in the receptacle for color comparison with said elements outside the receptacle.

16. In the method for detecting pH of vaginal or urethral moisture, the steps that include
   a) providing an elongated first carrier,
   b) providing a pH detector on the carrier at an end portion thereof,
   c) manipulating said carrier to effect exposure of said detector to vaginal or urethral moisture, thereby to cause said detector to exhibit a color change,
   d) providing a pH correlating color comparison measurement means, in sufficiently close association with said carrier and with said detector to allow visual comparison of the changed color exhibited by said detector with a pH correlated color provided by said measurement means,
   e) and including providing a longitudinally elongated receptacle for said carrier and detector, providing a support for said color comparison measurement means in association with the receptacle, said support defining a longitudinal window along which said color comparison measurement means is displayed in the form of bands, and manipulating said detector within the receptacle and along the window for visual color comparison with said bands.

17. The method of claim 16 wherein said bands are provided in two longitudinal rows, at laterally opposite sides of said window.

18. The method of claim 16 wherein said detector is provided to have a lateral dimension greater than width of the window, and said bands are provided to extend proximate window, and said detector is displaced longitudinally in proximate adjacency to the bands at opposite sides of the window.

19. In combination:
   a) a support package,
   b) a carrier and a pH detector on the carrier, the carrier removably support by the package,
   c) color comparison measurement elements carried by the package to allow their comparison with said pH detector after exposure of said detector to vaginal or urethral moisture the pH of which is to be determine,
   d) and wherein said package includes a longitudinally elongated receptacle for said detector, the package also including a support for said color comparison elements, in association with the receptacle, said support defining a longitudinal window along which said color comparison elements are displayed, whereby the detector may be manipulated within the receptacle and along the window for visual color comparison with said elements.

20. The combination of claim 19 wherein said elements extend in two longitudinal rows, at laterally opposite sides of said window.

21. The combination of claim 20 wherein said detector has lateral dimension matching or exceeding the width of the window and said elements extend into proximity to the window, whereby the detector may be displaced longitudinally in proximate adjacency to successive of said elements at opposite sides of the window.

22. In the method for detecting pH of vaginal or urethral moisture, the steps that include
   a) providing an elongated carrier,
   b) providing a pH detector in the form of a flat strip of material on the carrier,
   c) and manipulating said carrier to effect exposure of said detector to vaginal or urethral moisture, thereby to cause said detector to exhibit a color change,
   d) said package provided to include a receptacle for the elongated carrier and said detector, there being color comparison means provided in association with the receptacle and relative to which the carrier and detector are relatively longitudinally manipulatively movable, for color comparison with said color comparison means.

23. The method of claim 22 including providing said carrier to have longitudinal elongation for reception by the receptacle.

24. The method of claim 23 including providing said color comparison means to have close association with said receptacle to enable visual comparison of the color changed detector with said color comparison means.

25. The method of claim 24 including relatively moving said color changed detector and said color comparison means, in adjacent relation.

26. The method of claim 25 including providing said color comparison means to have different pH correlated colors in the direction of said relative movement.

* * * * *